(12) United States Patent
Baik

(10) Patent No.: US 7,686,784 B2
(45) Date of Patent: Mar. 30, 2010

(54) DISPOSABLE SYRINGE

(76) Inventor: Woo In Baik, 855 Guro-dong, Guro-gu (KR)

( * ) Notice: Subject to any disclaimer, the term of this patent is extended or adjusted under 35 U.S.C. 154(b) by 162 days.

(21) Appl. No.: 10/499,181

(22) PCT Filed: May 25, 2004

(86) PCT No.: PCT/KR2004/001241

§ 371 (c)(1),
(2), (4) Date: Jun. 8, 2005

(87) PCT Pub. No.: WO2004/103429

PCT Pub. Date: Dec. 2, 2004

(65) Prior Publication Data

US 2006/0111668 A1    May 25, 2006

(30) Foreign Application Priority Data

May 26, 2003   (KR) .................... 10-2003-0033400
Mar. 3, 2004   (KR) .................... 10-2004-0014356

(51) Int. Cl.
*A61M 5/00* (2006.01)

(52) U.S. Cl. ...................................... 604/110; 604/19
(58) Field of Classification Search ................ 604/110, 604/195, 111, 181, 192, 197–198, 218, 263, 604/246–242; 128/919
See application file for complete search history.

(56) References Cited

U.S. PATENT DOCUMENTS 5,171,300 A * 12/1992 Blake et al. ................ 604/110
6,391,008 B1   5/2002 Tsai
6,488,657 B1 * 12/2002 Lo ............................. 604/110

* cited by examiner

*Primary Examiner*—Kevin C Sirmons
*Assistant Examiner*—Phillip Gray
(74) *Attorney, Agent, or Firm*—Sherr & Vaughn, PLLC

(57) ABSTRACT

A disposable syringe, which is enhanced for a safer use, is disclosed. The disposable syringe includes a cylinder having both ends open, an adapter tube inserted in one side of the cylinder, an insertion tube inserted in the adapter tube, and allowing the adapter tube to be in airtight contact with an inner circumference of the cylinder, and a piston inserted in the cylinder.

16 Claims, 15 Drawing Sheets

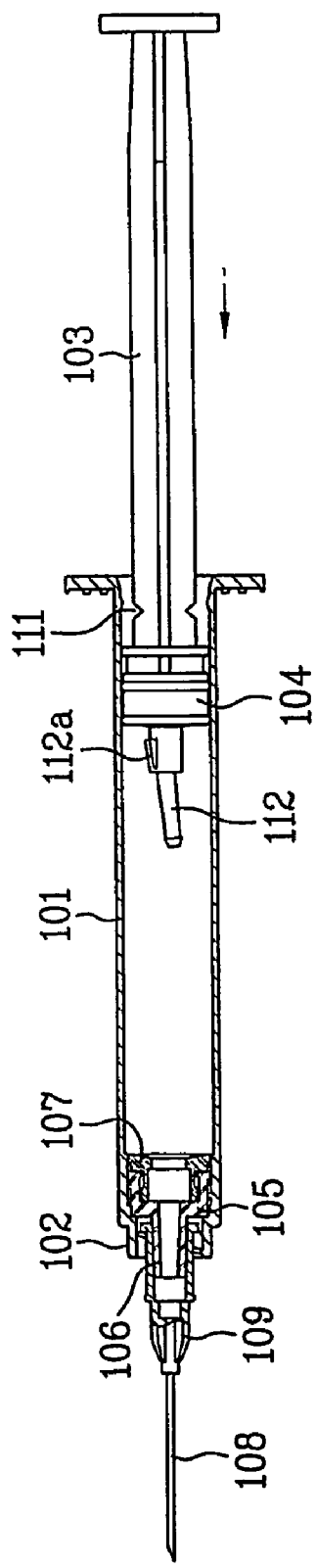
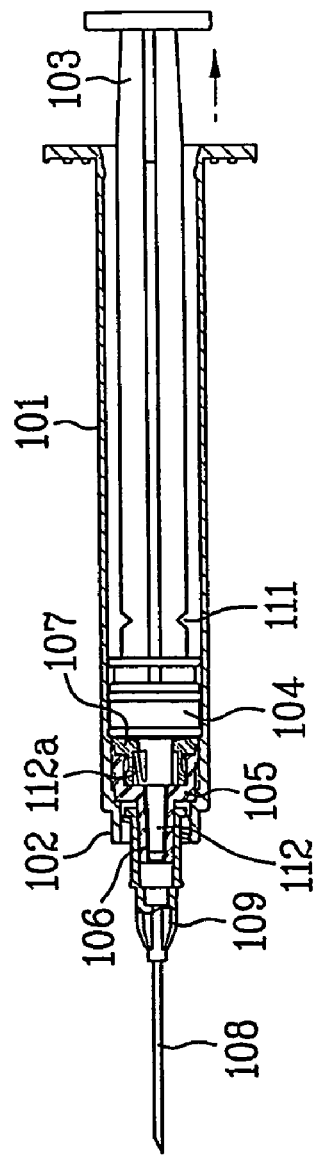
FIG. 9A
FIG. 9B

DISPOSABLE SYRINGE

CROSS-REFERENCE TO RELATED APPLICATIONS

This application claims the benefit of Korean Application Nos. 2004-0014356, filed Mar. 3, 2004, and P-2003-033400, filed on May 26, 2003, which are hereby incorporated by reference as if fully set forth herein.

BACKGROUND OF THE INVENTION

1. Field of the Invention

The present invention relates to a syringe, and more particularly, to a disposable syringe. Although the present invention is suitable for a wide scope of applications, it is particularly suitable for providing a safer disposable syringe with enhanced safety measures.

2. Discussion of the Related Art

Generally, a syringe is a medical device used to inject an injection liquid (e.g., medication) into the body (or veins) of a medical patient. Also, the syringe is typically disposable after use, thereby preventing a third person from being infected by diseases carried by the patient. A related art disposable syringe will now be described with reference to the accompanying drawings.

FIG. 1 illustrates an exploded perspective view of a disposable syringe according to a first embodiment of the related art.

Referring to FIG. 1, the related art disposable syringe is formed of a cylinder 1 having an empty space therein, and a coupling tube 2 formed at a fore end of the cylinder 1 and having a step difference. The related art disposable syringe also includes a plunger 3 moving within the cylinder 1 in back-and-forth movements along the length of the cylinder 1. A piston 4 is formed at the fore end of the plunger 3 and moves along with the plunger 3 in airtight contact with the inner surface of the cylinder 1.

A syringe needle holder 5 is detachably fixed onto the external surface of the coupling tube 2 formed on the cylinder 1. A syringe needle 6 is fixed in the syringe needle holder 5. Also, a protective cap 7 is attached to completely cap the syringe needle holder 5 and the syringe needle 6.

FIG. 2A illustrates an exemplary process step of sucking the injection liquid into the syringe.

Referring to FIG. 2A, the protective cap 7 protecting the syringe needle 6 is first detached from the syringe needle holder 5. Then, the plunger 3 inserted into the empty space of the cylinder 1 is pushed forward to the fore end of the cylinder 1. Then, the end of the syringe needle 6 is inserted and dipped into an injection liquid container (not shown). Thereafter, the plunger 3 having the piston 4 fixed thereon is pulled back, thereby creating a suction force within the empty space of the cylinder 1. Due to the suction force, the injection liquid is sucked into the cylinder 1 through the syringe needle 6 fixed to the syringe needle holder 5, thereby filling the empty space of the cylinder 1.

FIG. 2B illustrates an exemplary process step of injecting the injection liquid to a patient.

Referring to FIG. 2B, a user sticks the syringe needle 6 into a patient's skin, and then pushes the plunger 3 to move the piston 4 towards the fore end of the cylinder 1. At this point, a pressure is formed within the empty space of the cylinder 1, more specifically, at the fore end of the piston 4 (shown as the left side area in FIG. 2B). Accordingly, due to the pressure of the piston 4, the injection liquid filled in the empty space of the cylinder 1 flows out of the cylinder 1 through the coupling tube 2 formed at the edge of the cylinder 1.

The injection liquid passing through the coupling tube 2 then continues to flow through the syringe needle 6 fixed in the syringe needle holder 5, thereby being injected into the skin and veins of the patient. During this process, because the syringe needle holder 5 is fixed to the coupling tube 2 by interference fit, the injection liquid does not leak from the coupling tube 2 and the syringe needle holder 5.

Meanwhile, after the use of the syringe, the protective cap 7 is safely and completely fixed to the syringe needle holder 5 to cap and protect the syringe needle 6, so as to safely dispose of the used syringe.

The above-described disposable syringe is advantageous in that the injection liquid does not leak from the syringe during the injection process. However, when recapping the protective cap 7 onto the syringe needle holder 5 after use, the user or a third person may be injured by the syringe needle. Also, when the protective cap is detached from the syringe while disposing medical waste, another third person (i.e., a person handing the medical waste) may also be injured by the syringe needle.

Therefore, in order to prevent such small accidents from occurring, manufacturers of medical instruments, apparatuses, and devices are developing new types of disposable syringes with enhanced safety functions.

FIG. 3 illustrates an exploded perspective view of a disposable syringe according to a second embodiment of the related art.

The related art syringe includes a cylinder 11 having a coupling tube 12 formed to have a step difference at the fore end edge of the cylinder 11, and a plunger 13 having a piston 14 fixed thereto. An O-ring 19 is formed at the inner circumference of the coupling tube 12 to be fixed airtight to the syringe needle holder 15. Also, a flange 15a is formed at the back end and on the outer circumference of the syringe needle holder 15.

The cylinder 11 is formed to have one end and the other end connected to each other and forming an empty space therein. The coupling tube 12 having a step difference is formed at the fore end of the cylinder 11. Finally, a protective cap 17 is detachably fixed to the outer surface of the coupling tube 12, so as to cap and protect the syringe needle 16.

The plunger 13 moving within the cylinder 11 in back-and-forth movements along the length of the cylinder 11 is inserted into the empty space of the cylinder 11. The piston 14 is formed at the fore end of the plunger 13, so as to move along the cylinder 11 in airtight contact with the inner surface of the cylinder 11, thereby providing pressure or a suction force. In addition, a connecting part 13a corresponding to a connective projection of the syringe needle holder 15 is formed at the fore end of the plunger 13. Finally, a cutting grove 18 is formed on the plunger 13 near the piston 14, thereby enabling the plunger 13 to be easily broken.

The syringe needle holder 15 is inserted into the cylinder through the empty space, so as to be exposed to the fore end of the coupling tube 12. In order to be more stably fixed to the coupling tube 12, a contacting surface should be maintained between the syringe needle holder 15 and the coupling tube 12. However, if the syringe needle holder 15 is fixed to the coupling tube 12 by interference fit, the syringe needle holder 15 may not be able to be pulled into the empty space of the cylinder after the injection. Therefore, a fine gap should be maintained when fixing the syringe needle holder 15 to the coupling tube 12. Due to the step difference between the cylinder 11 and the coupling tube 12, the flange 15a comes into contact with the inner step formed inside the cylinder 11.

The O-ring 19 is fixed to the inner circumference of the coupling tube 12, thereby preventing injection liquid from leaking through the fine gap between the coupling tube 12 and the syringe needle holder 15. More specifically, the O-ring 19 maintains an airtight seal between the coupling tube 12 and the syringe needle holder 15.

FIG. 4 illustrates a perspective view of a syringe needle holder and the plunger being detached from the disposable syringe according to the second embodiment of the related art.

A pair of projections 15b facing into each other is formed in the inner circumference and at the back end of the needle holder 15. A connecting part 13a is formed at the fore end of the plunger 13, so as to be connected with the projections 15b when the plunger 13 is pushed to the fore end of the cylinder 11. Also, each of the connecting part 13a and the projections 15b has an inclined surface, so as to minimize interference caused by contact when the fore end of the plunger 13 is inserted to the syringe needle holder 15.

FIGS. 5A to 5E illustrate cross-sectional views showing usage steps of the disposable syringe according to the second embodiment of the related art.

In order to inject the injection liquid to a patient, the injection liquid should first be sucked onto the empty space of the cylinder. However, since the process step of sucking the injection liquid into the syringe is the same as that described in FIG. 2A, the description will be omitted for simplicity.

FIG. 5A illustrates the empty space of the cylinder 11 is filled with an injection liquid, shown as the left side area of the syringe. The process of injecting the injection liquid to the patient is identical to that described in FIG. 2B, and therefore, the description of the same will also be omitted for simplicity.

FIGS. 5B and 5C illustrate the completion of the injection and the process step of pulling the syringe needle holder back into the cylinder.

Referring to FIGS. 5B and 5C, when the injection of the injection liquid is completed, the syringe needle holder 15 is inserted in the coupling tube 12 formed on the cylinder 11. At this point, the flange 15a, which is formed at the back end and on the outer circumference of the syringe needle holder 15, comes into contact with the inner step formed inside the cylinder 11 due to the step difference between the cylinder 11 and the coupling tube 12. And so, the flange 15a limits further forward movement of the syringe needle holder 15.

Meanwhile, after the injection is completely, the syringe needle 16 is pulled out of the patient's skin. Then, the plunger 13 is pulled back in the direction opposite to the patient (i.e., in a backward direction), the syringe needle holder 15 is also pulled back along with the plunger 13. This is because the connecting part 13a is connected to the projections 15b of the syringe needle holder 15.

Then, the plunger 13 is pulled further towards the back end of the cylinder 11, so that the syringe needle holder 15 is completed pulled into the cylinder 11. The syringe needle holder 15 is held by the connecting part 13a of the plunger 13. In other words, since the outside diameter of the flange 15a is smaller than the inside diameter of the cylinder 11, the syringe needle holder 15 is hung onto the fore end of the plunger 13. Therefore, due to an eccentric center of gravity, the syringe needle holder 15, having the connecting point between the holder 15 and the fore end of the plunger 13 as its support point, is inclined downwards (i.e., towards the gravitational direction). At this point, only the fore end of the syringe needle 16 comes into contact with the inner surface of the cylinder 11. Moreover, a constant inclination angle is maintained between the contacting surface of the cylinder 11 and the syringe needle holder 15.

FIGS. 5D and 5E illustrate process steps of preventing the syringe needle holder from being extracted from the cylinder.

Referring to FIGS. 5D and 5E, the cutting groove 18 formed on the plunger 13 is pulled back near the outside of the cylinder 11. Then, the plunger 13 is repeatedly pressed downwards in a direction perpendicular to the plunger 13, thereby breaking the plunger 13 along the cutting groove 18 formed thereon. Subsequently, the broken portion of the plunger 13 is placed to be parallel to and facing into the fore end of the cylinder 11. Then, when the broken portion of the plunger 13 is inserted through the coupling tube 12, the fore end of the cylinder 11 is blocked, thereby preventing the syringe needle holder 15 held within the cylinder 11 from falling or slipping out of the cylinder 11.

However, the above-described related art disposable syringe is disadvantageous in that it requires and uses an O-ring.

The O-ring is sensible to even the slightest external pressure, thereby being easily deformed. Therefore, when the O-ring fails to be stably inserted into the coupling tube, the syringe can become deficient.

Also, in order to reduce deficiency in disposable syringes using the O-ring, a wide range of complex auxiliary fabrication devices are required in the fabrication line, thereby causing an increase in the product cost.

Finally, since the deficiency in the O-ring cannot be recognized through the naked eye, when using a syringe fabricated with the deficient O-ring, the injection liquid may leak from the syringe during the injection process.

SUMMARY OF THE INVENTION

Accordingly, the present invention is directed to a disposable syringe that substantially obviates one or more problems due to limitations and disadvantages of the related art.

An object of the present invention is to provide a disposable syringe having reduced product deficiency, thereby allowing safer usage of the disposable syringe.

Another object of the present invention is to provide a disposable syringe that does not require auxiliary fabrication devices in the fabrication line in order to reduce deficiency in disposable syringes, thereby reducing the fabrication cost.

A further object of the present invention is to provide a disposable syringe allowing the deficiency of the adapter tube and the insertion tube, if any, to be easily detected through the naked eye upon the assembly process of the disposable syringe, thereby increasing product reliability upon the usage of the disposable syringe.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a disposable syringe includes a cylinder having both ends open, an adapter tube inserted in one side of the cylinder, an insertion tube inserted in the adapter tube, and allowing the adapter tube to be in airtight contact with an inner circumference of the cylinder, and a piston inserted in the cylinder.

It is preferable that the adapter tube includes a small diameter part, and a large diameter part having an inside diameter relatively larger than the small diameter part, and that the insertion tube includes a first contacting part being in airtight contact with an inner circumference of the large diameter part of the adapter tube, and an insertion part being inserted in the small diameter part. It is also preferable that the syringe according to the present invention further includes a second contacting part extendedly formed at a back end of the first contacting part and contacting the inner circumference of the cylinder.

It is preferable that a second connecting part is formed at the small diameter part of the adapter tube, and a second projection corresponding to the second connecting part of the adapter tube is formed at the insertion part of the insertion tube. And, it is preferable that the second projection of the insertion tube is formed only at a fore end portion of the insertion tube. It is also preferable that the second projection of the insertion tube is formed to be inclined towards a fore end of the insertion tube.

It is preferable that a first connecting part is formed on an inner circumference and at a back end of the insertion tube, and a first projection corresponding to the first connecting part of the insertion tube is formed at a fore end of the piston. It is also preferable that one of the first connecting part of the insertion tube and the first projection of the piston is formed to be inclined. It is preferable that an outside diameter of the first contacting part of the insertion tube is larger than an inside diameter of the large diameter part of the adapter tube.

Also, it is preferable that a projection is formed on an outer circumference of the adapter tube, and a groove corresponding to the projection of the adapter tube is formed on the inner circumference of the cylinder. It is preferable that at least one of the adapter tube and the insertion tube is formed of an elastic material. In addition, it is preferable that a projected part is formed on the outer circumference of the adapter tube, and an insertion groove corresponding to the projected part of the adapter tube is formed on the inner circumference of the cylinder.

And, it is preferable that an injection liquid outlet tube is extendedly formed at a fore end of the adapter tube. Herein, it is preferable that a syringe needle holder is coupled to the injection liquid outlet tube.

Also, it is preferable that a coupling tube is formed at a fore end of the cylinder, a projection is formed on an inner circumference of the coupling tube, and a flange corresponding to the projection of the coupling tube is formed on the syringe needle holder. And, it is preferable that a pressurization part inserted in the injection liquid outlet tube is eccentrically formed at the fore end of the piston. Herein, it is also preferable that the pressurization part is formed of an elastic material.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings:

FIGS. 9A to 9F illustrate cross-sectional views showing usage steps of the disposable syringe according to the first embodiment of the present invention;

DETAILED DESCRIPTION OF THE INVENTION

Figure 1:
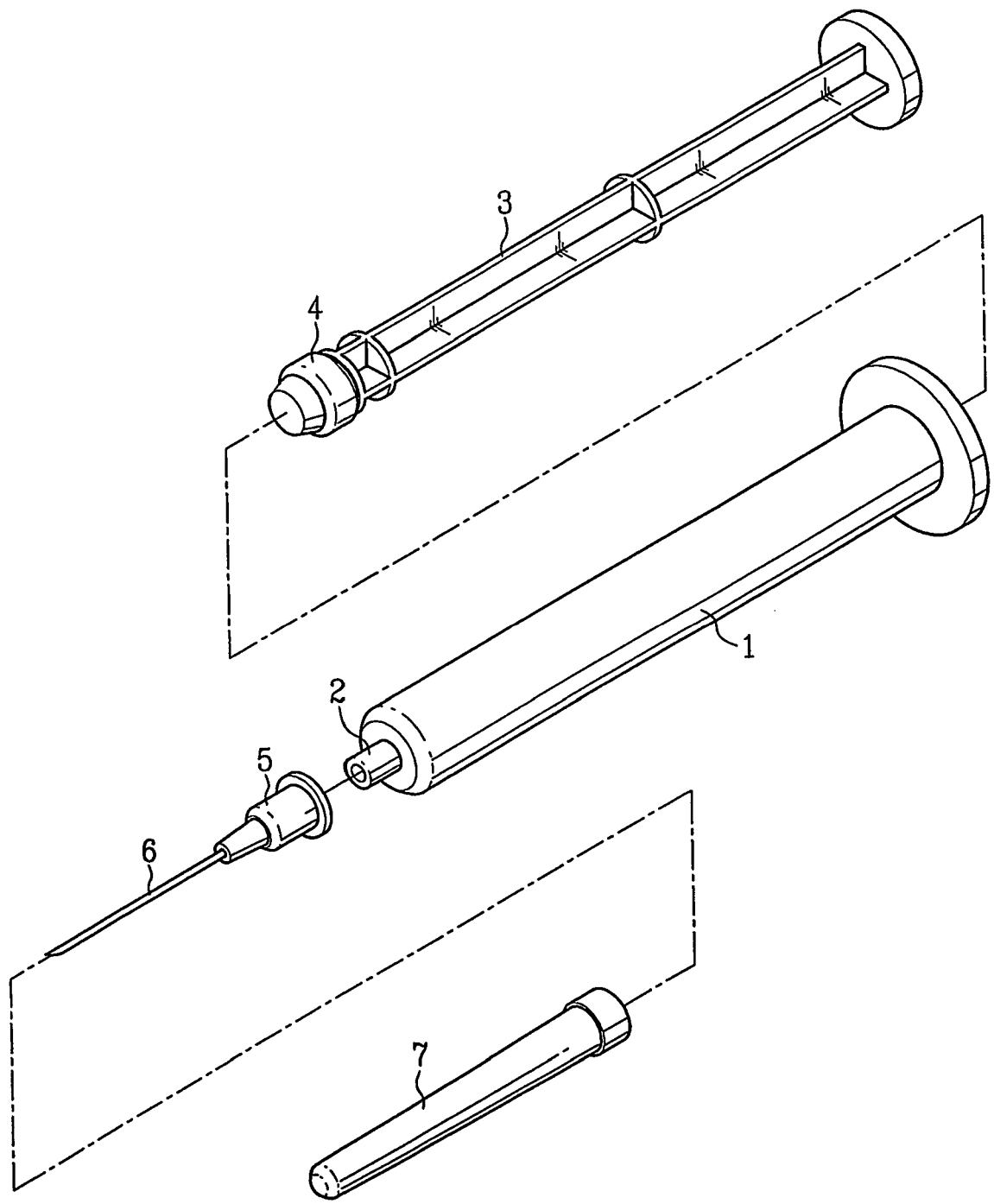
FIG. 1 illustrates an exploded perspective view of a disposable syringe according to a first embodiment of the related art.
Figure 2A:
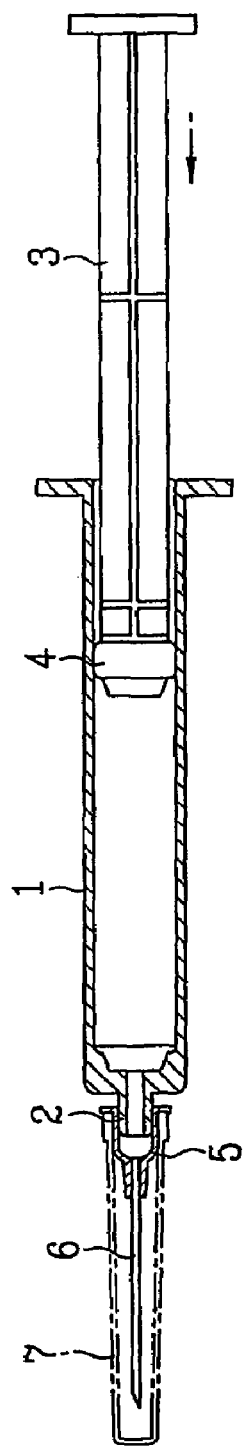
FIGS. 2A and 2B illustrate a cross-sectional view showing a usage of the disposable syringe according to the first embodiment of the related art.
Figure 2B:
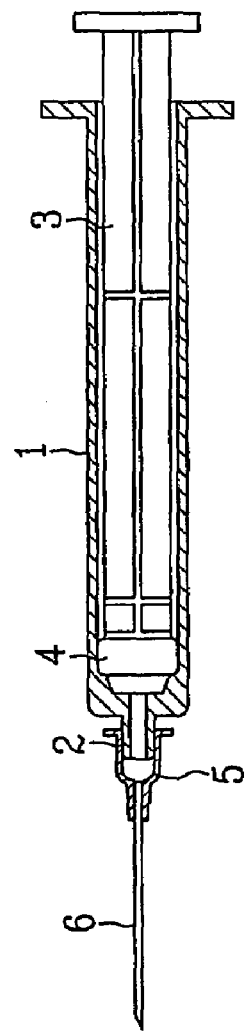
Figure 3:
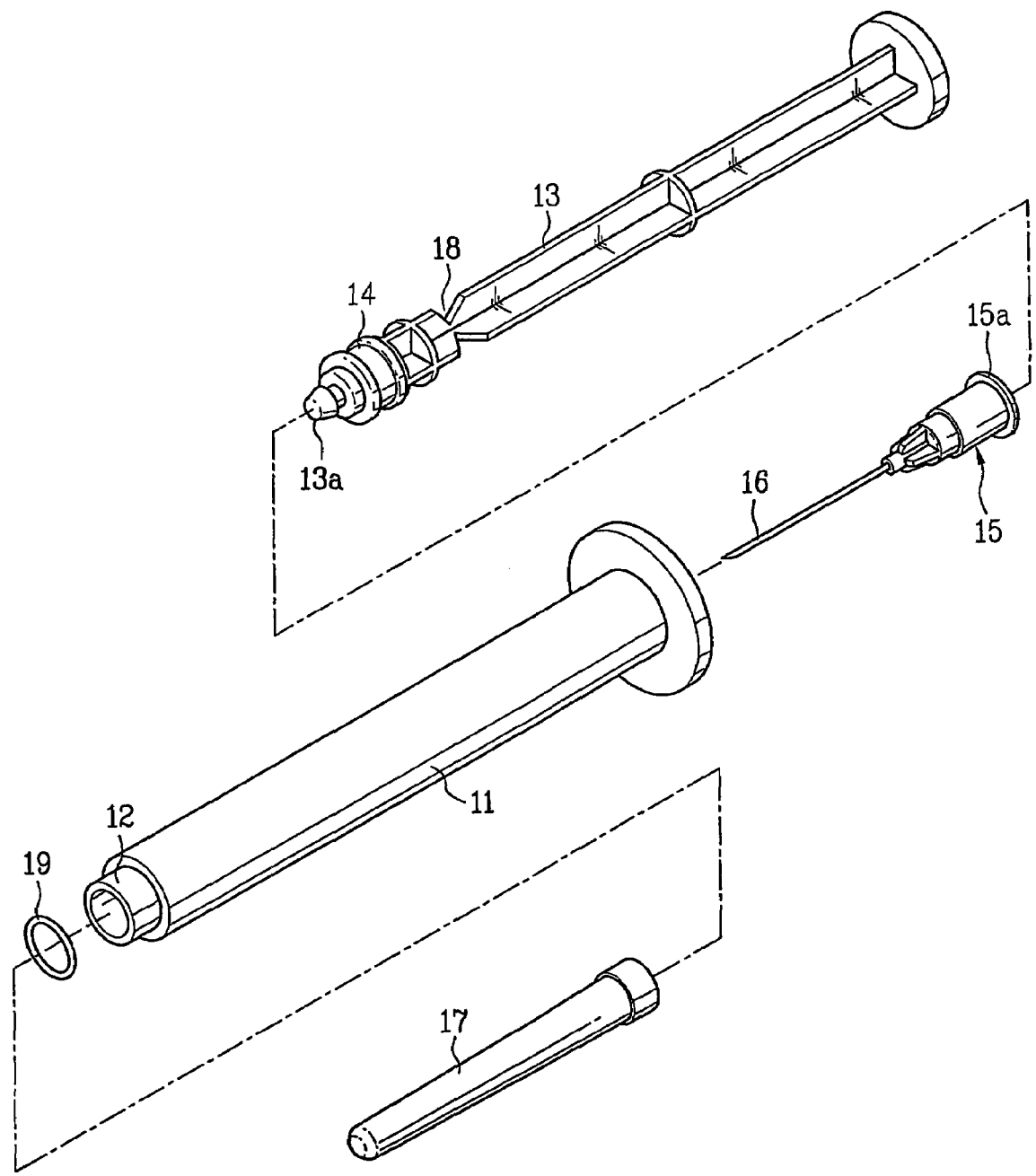
FIG. 3 illustrates an exploded perspective view of a disposable syringe according to a second embodiment of the related art.
Figure 4:
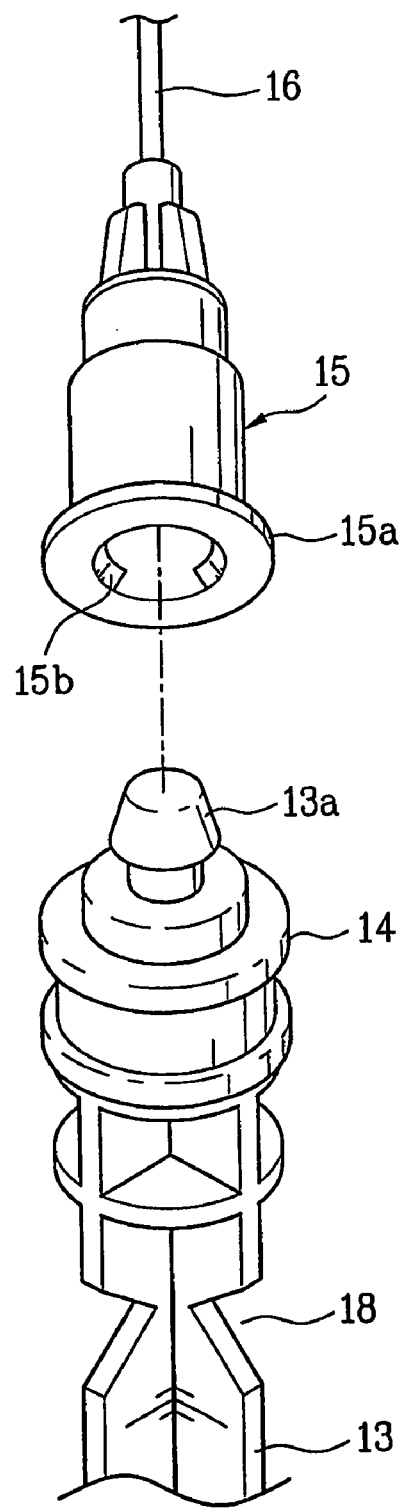
FIG. 4 illustrates a perspective view of a syringe needle holder and plunger being detached from the disposable syringe according to the second embodiment of the related art.
Figure 5A:
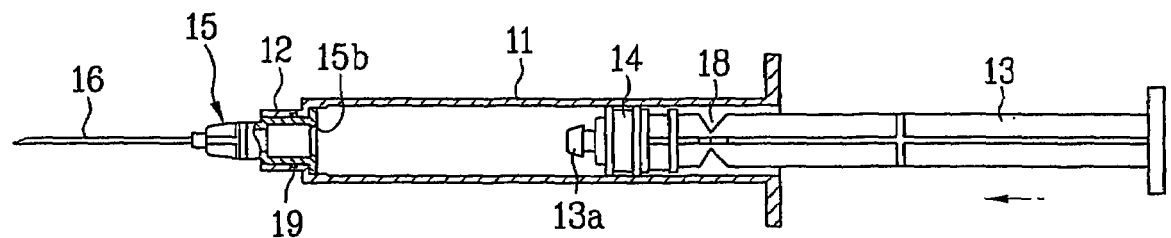
FIGS. 5A to 5E illustrate cross-sectional views showing usage steps of the disposable syringe according to the second embodiment of the related art.
Figure 5B:
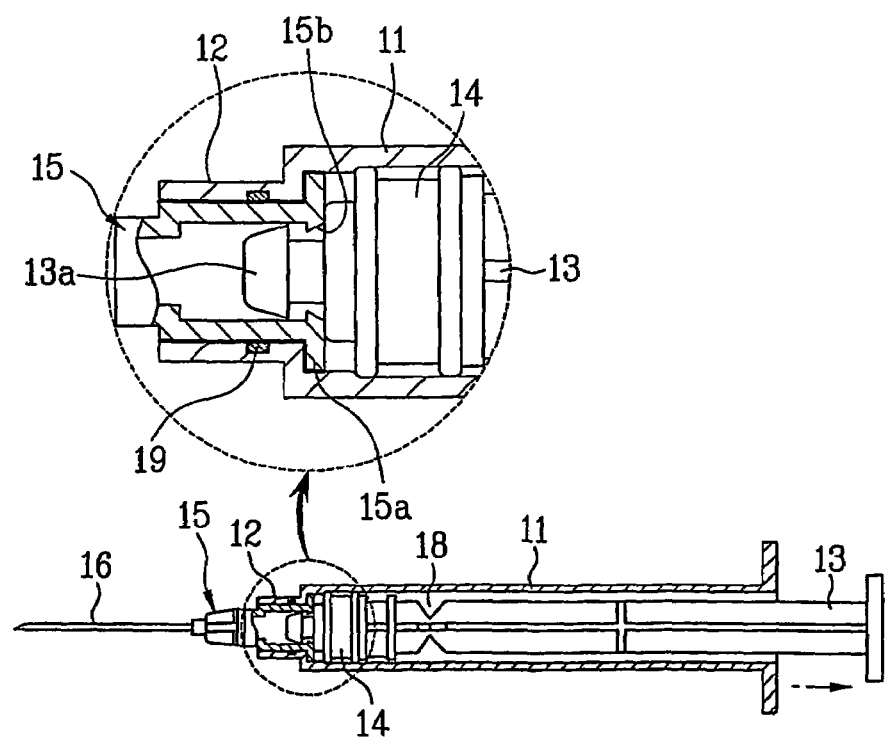
Figure 5C:
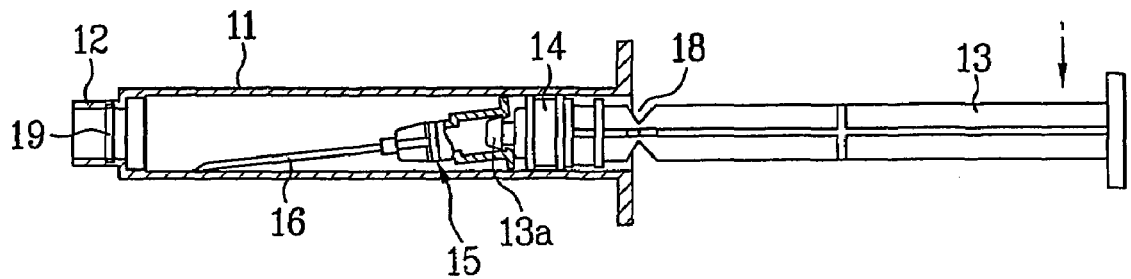
Figure 5D:
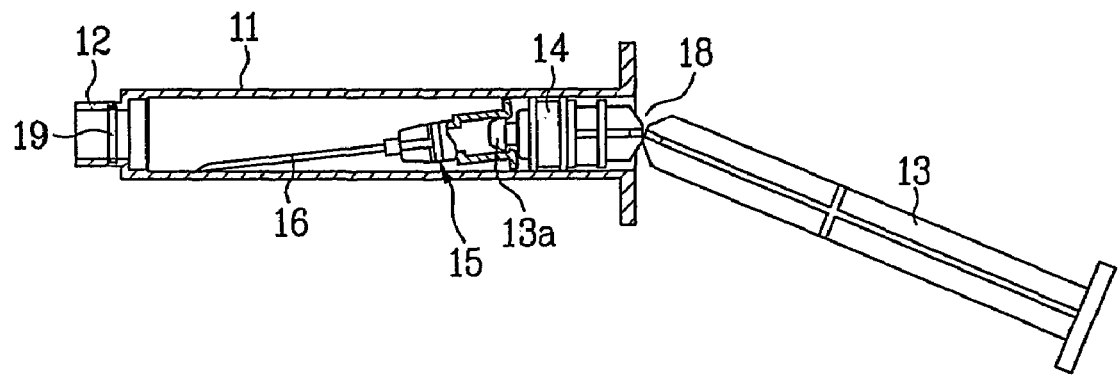
Figure 5E:
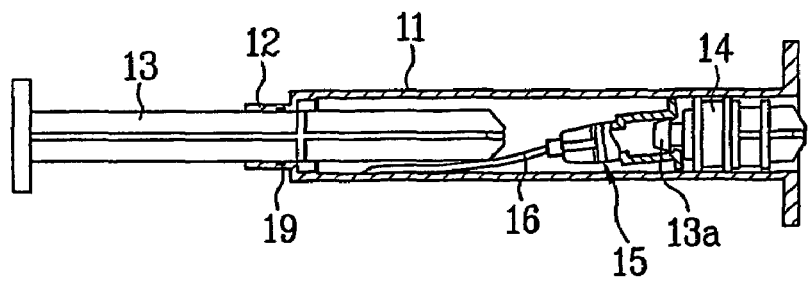

Reference will now be made in detail to the preferred embodiments of the present invention, examples of which are illustrated in the accompanying drawings. Wherever possible, the same reference numbers will be used throughout the drawings to refer to the same or like parts.

The disposable syringe according to a first embodiment of the present invention will now be described in detail with reference to FIGS. 6 to 8 and FIGS. 9A to 9F.

The disposable syringe according to the present invention will now be briefly described as follows.

An adapter tube 105 is inserted in one side of the cylinder 101 having both ends open. And, an insertion tube 107 is inserted in the adapter tube 105, so as to be in airtight contact with an inner circumference of the cylinder 101. A plunger having a piston 104 for pressurizing an injection liquid is also inserted in the cylinder 101.

The description for each assembly part of the disposable syringe according to the present invention will now follow.

The adapter tube includes a small diameter part 105$f$, and a large diameter part 105$g$ having an inside diameter relatively larger than the small diameter part. Also, the insertion tube includes a first contacting part 107$g$ being in airtight contact with an inner circumference of the large diameter part of the adapter tube, and an insertion part 107$f$ being inserted in the small diameter part. In addition, it is preferable that a second contacting part 107$h$ is extendedly formed at a back end of the first contacting part and contacting the inner circumference of the cylinder.

It is preferable that a second connecting part 105$a$ is formed at the small diameter part of the adapter tube, and a second projection 107$b$ corresponding to the second connecting part of the adapter tube is formed at the insertion part of the insertion tube. And, it is preferable that the second projection of the insertion tube is formed only at a fore end portion of the insertion tube. Moreover, it is preferable that the second projection of the insertion tube is formed to be inclined towards a fore end of the insertion tube. It is preferable that an outside diameter of the first contacting part of the insertion tube is larger than an inside diameter of the large diameter part of the adapter tube, and that at least one of the adapter tube and the insertion tube is formed of an elastic material.

It is preferable that a first connecting part 107a is formed on an inner circumference and at a back end of the insertion tube, and a first projection 112a corresponding to the first connecting part of the insertion tube is formed at a fore end of the piston. It is also preferable that one of the first connecting part of the insertion tube and the first projection of the piston is formed to be inclined.

Also, it is preferable that a projection 105b is formed on an outer circumference of the adapter tube, and a groove 101a corresponding to the projection of the adapter tube is formed on the inner circumference of the cylinder. In addition, it is preferable that a projected part 105c is formed on the outer circumference of the adapter tube, and an insertion groove 101b corresponding to the projected part of the adapter tube is formed on the inner circumference of the cylinder.

And, it is preferable that an injection liquid outlet tube 106 is extendedly formed at a fore end of the adapter tube, and that a syringe needle holder 109 is coupled to the injection liquid outlet tube. It is also preferable that a coupling tube 102 is formed at a fore end of the cylinder, a projection 102a is formed on an inner circumference of the coupling tube, and a flange 109a corresponding to the projection of the coupling tube is formed on the syringe needle holder.

Finally, it is preferable that a pressurization part 112 inserted in the injection liquid outlet tube is eccentrically formed at the fore end of the piston, and that the pressurization part is formed of an elastic material.

Figure 6:
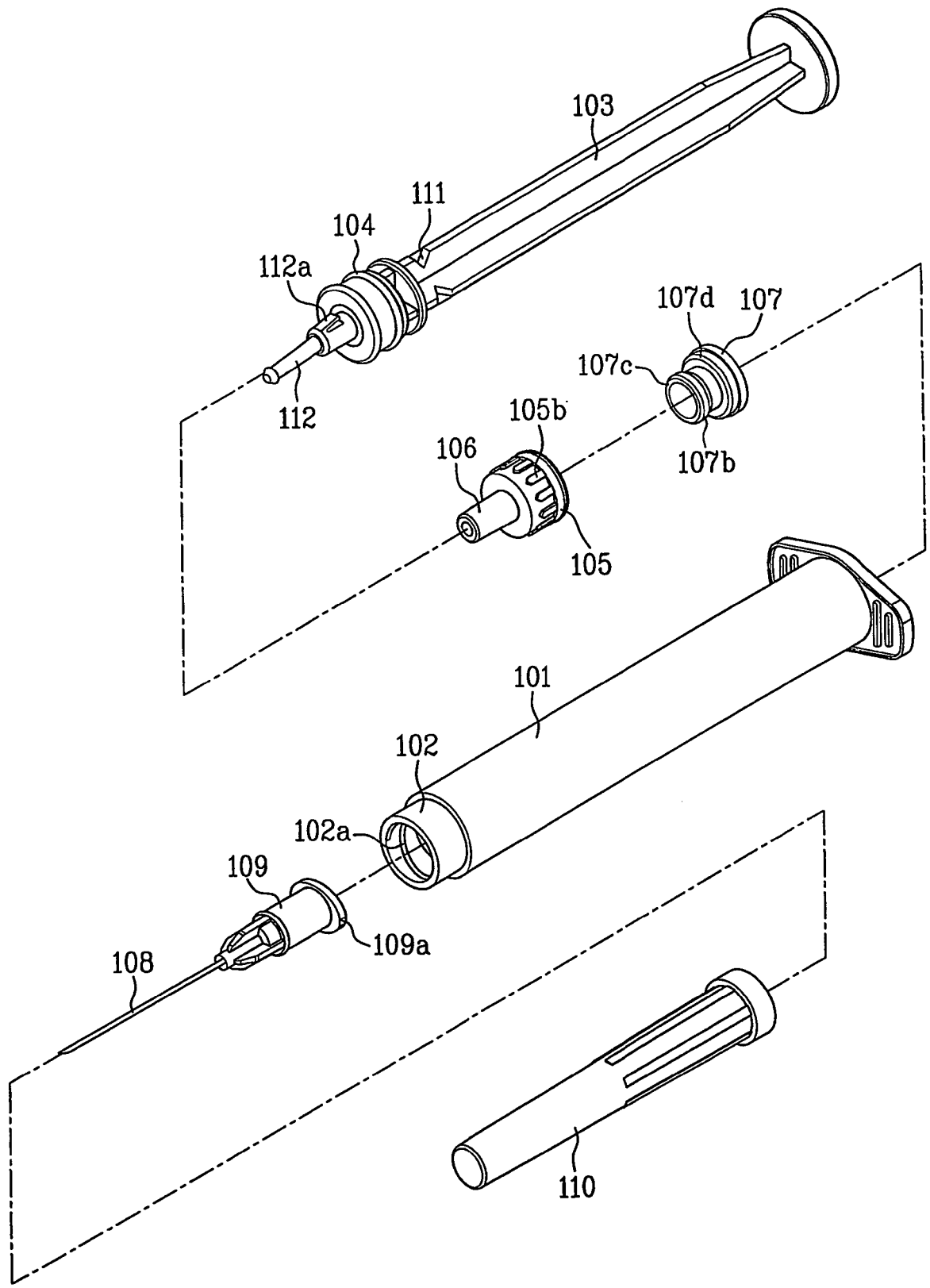
FIG. 6 illustrates an exploded view of a disposable syringe according to a first embodiment of the present invention.

FIG. 6 illustrates an exploded view of a disposable syringe according to the first embodiment of the present invention.

Referring to FIG. 6, the syringe according to the present invention includes a cylinder 101 having a coupling tube 102 formed thereon, an adapter tube 105 being inserted into the inside of the cylinder 101, and an insertion tube 107 being inserted into the adapter tube 105. The syringe also includes a plunger 103 having a piston 104 and a pressurization part 112 formed thereon, and a syringe needle holder 109 coupled to the coupling tube 102.

The cylinder 101 is formed to have one end and the other end connected to each other and forming an empty space therein. The coupling tube 102 having a step difference is formed at the fore end of the cylinder 101. And, a spiral projection 102a is formed at the edge portion of the inner circumference of the coupling tube 102.

The adapter tube 105 is inserted in the inner portion of the fore end of the cylinder 101. A plurality of fastening projections 105b are formed on the outer surface of the adapter tube 105 along the circumference and spaced apart from one another at a set distance. Then, an injection liquid outlet tube 106, having a diameter smaller than that of the adapter tube 105, is formed at the central portion of the fore end of the adapter tube 105.

The insertion tube 107 is inserted at a set portion inside the adapter tube 105, so as to apply pressure to the adapter tube 105 towards the cylinder 101, thereby maintaining an airtight condition between the adapter tube 105 and the cylinder 101. A second projection 107b is formed on the fore end outer circumference of the insertion tube 107. Also, a first tapered inclined surface 107c, having an outside diameter decreasing from the back end towards the fore end, is formed on the fore end edge of the insertion tube 107. Moreover, a second tapered inclined surface 107d, having an outside diameter decreasing from the back end towards the fore end, formed on the back end outer circumference of the insertion tube 107.

A pressurization part 112 is formed on the fore end of the plunger 103. The pressurization part is inserted in the injection liquid outlet tube 106 formed on the adapter tube 105. And, a first projection 112a is formed on the back end portion of the pressurization part 112. The piston 104 is formed at the fore end of the plunger 103, so as to move along the cylinder 101 in airtight contact with the inner surface of the cylinder 101, thereby providing pressure or a suction force. In addition, a cutting grove 111 is formed on the plunger 103 near the piston 104, thereby enabling the plunger 103 to be easily broken.

The syringe needle 108 is fixed onto the fore end of the syringe needle holder 109, and an oval flange 109a is formed on the back end outer surface of the syringe needle holder 109. A protective cap 110 is detachably fixed to the syringe needle holder 109 for capping and protecting the syringe needle 108.

Figure 7:
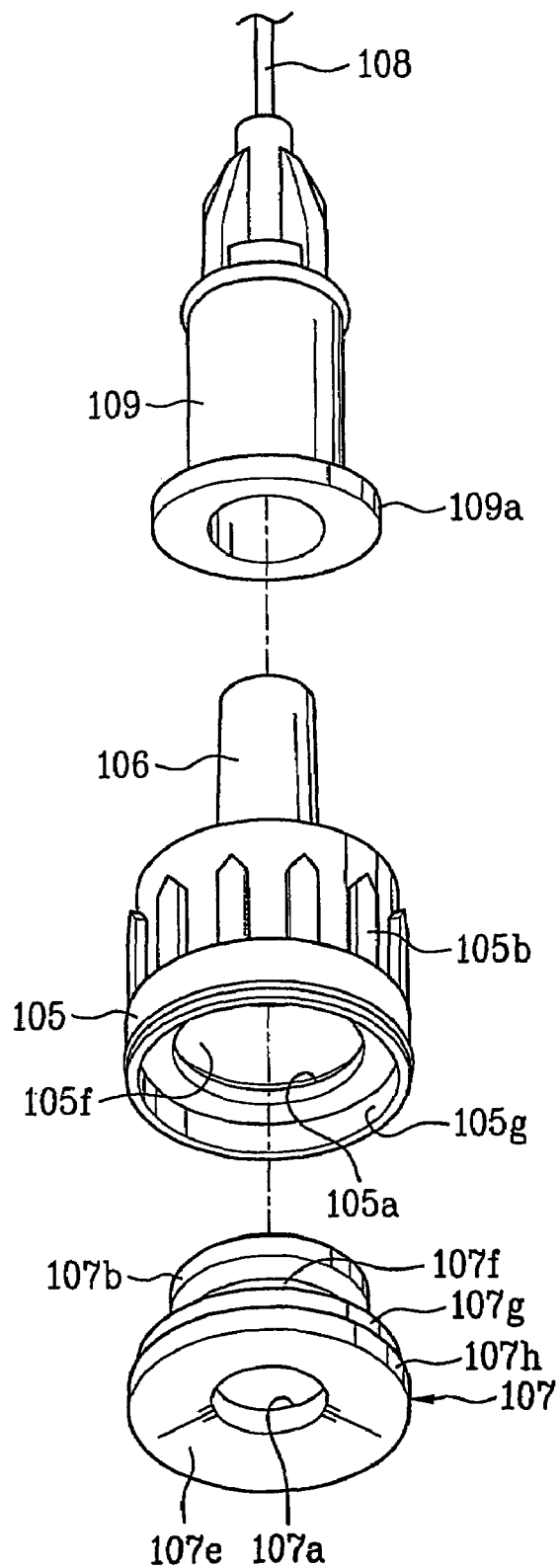
FIG. 7 illustrates a perspective view of the main parts of the disposable syringe according to the first embodiment of the present invention.

FIG. 7 illustrates in detail the inner structure of the adapter tube and the insertion tube of the disposable syringe according to the first embodiment of the present invention.

Referring to FIG. 7, a first connecting part 107a is formed along the inner circumference of the insertion tube 107. The first connecting part 107a is connected with the first projection 112a formed on the pressurization part 112. In other words, as the pressurization part formed on the plunger is pulled backwards, the insertion tube 107 is also pulled backwards accordingly. Also, an inclined surface 107e is formed on the back end edge of the insertion tube 107. The inclined surface 107e is identical to that of the fore end of the piston 104, thereby allowing the injection liquid to be completely injected and flown out. A second connecting part 105a is formed along the inner circumference of the adapter tube 105. The second connecting part 105a is connected with the second projection 107b formed on the insertion tube 107. In other words, when the insertion tube 107 is moved backwards, the adapter tube 105 is also moved backwards accordingly.

The assembly process of the disposable syringe according to the first embodiment of the present invention will now be described in detail with reference to FIGS. 6 to 8.

Figure 8:
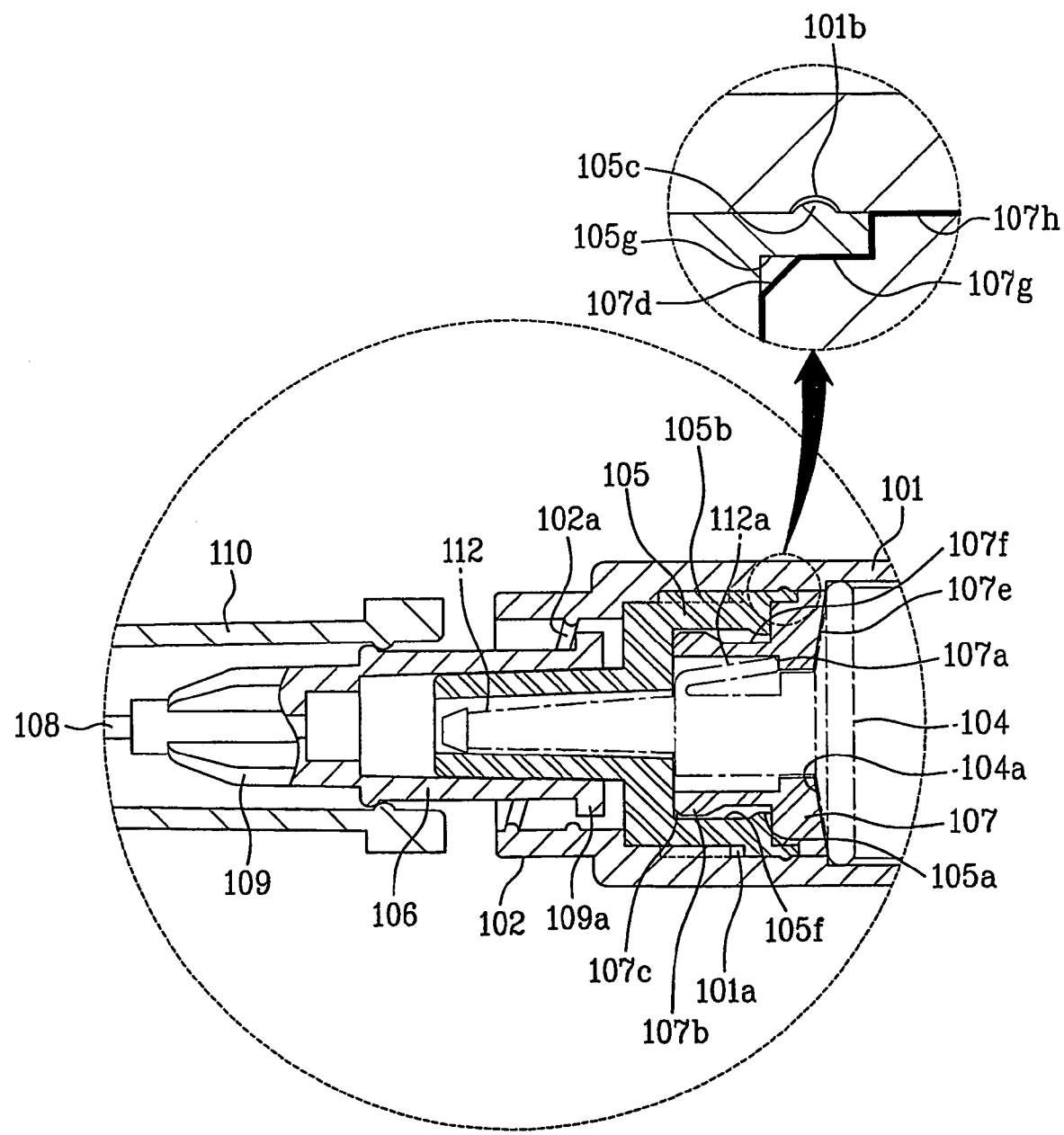
FIG. 8 illustrates a cross-sectional view of the main parts of the disposable syringe according to the first embodiment of the present invention.

Referring to FIGS. 6 to 8, the injection liquid outlet tube 106 formed on the adapter tube 105 faces the back end side of the cylinder 101. And, when the adapter tube 105 is moved forward, the adapter tube 105 is inserted and fixed within the empty space of the cylinder 101. At this point, the plurality of fastening projections 105b, which is formed on the outer surface of the adapter tube 105 along the circumference and spaced apart from one another at a set distance, is inserted and fastened to a plurality of fastening grooves 101a formed on the inner circumference of the cylinder 101.

Then, the insertion tube 107 is inserted into the empty space of the cylinder 101 from the back end thereof, and the insertion tube 107 is then pushed and moved forward. At a certain point, the insertion tube 107 is inserted and fixed to the inner circumference of the adapter tube 105. The second projection 107b on the outer circumference of the insertion tube 107 is connected to the second connecting part 105a formed on the inner circumference of the adapter tube 105, thereby resulting in a first interference. This is because, at the point of connection, the outside diameter of the insertion tube 107 is greater than the inside diameter of the adapter tube 105. Thereafter, when the insertion tube 107 pushed further towards the fore end of the cylinder 101, the second projection 107b overcomes the interfering force of the second connecting part 105a. This is because a first tapered inclined surface 107c, having an outside diameter decreasing from the back end towards the fore end, is formed on the fore end edge of the insertion tube 107, and also because the insertion tube 107 is formed of an elastic material.

Meanwhile, as the insertion tube 107 is pushed even further towards the fore end of the cylinder 101, a second interference occurs between the back end outer circumference of the insertion tube 107 and the back end inner circumference of the adapter tube 105. In other words, the insertion tube 107 and the adapter tube 105 are connected by interference fit. This is because the outside diameter of the insertion tube 107 is relatively greater than the back end inside diameter of the adapter tube 105. The insertion tube 107 is pushed further down to be completely inserted in the adapter tube 105. This is because a second tapered inclined surface 107d, having an outside diameter decreasing from the back end towards the fore end, is formed on the fore end edge of the insertion tube 107, and also because the insertion tube 107 is formed of an elastic material.

When the insertion tube 107 is completely inserted into the adapter tube 105, the insertion tube 107 applies pressure on the back end portion of the adapter tube 105 towards the cylinder 101. Therefore, an airtight condition can be maintained between the adapter tube 105 and the cylinder 101. At this point, a semi-circular projected part 105c formed along the back end circumference of the adapter tube 105 is fixed to a semi-circular insertion groove 101b formed on the inner surface of the cylinder 101. Accordingly, the projected part 105c acts as a packing means enhancing the airtight condition between the adapter tube 105 and the cylinder 101, thereby preventing the injection liquid from leaking between the adapter tube 105 and the cylinder 101 under any possible circumstances.

As described above, the adapter tube 105 is inserted into the empty space of the cylinder 101, and the insertion tube 107 is inserted and fixed to the adapter tube 105. Then, the piston 104 is provided within the empty space of the cylinder 101. And, the plunger 103 having the cutting groove 111 formed thereon in inserted into the cylinder 101. Thereafter, the syringe needle holder 109 is inserted and fixed to the injection liquid outlet tube 106, which is then attached to the coupling tube 102 formed in the cylinder 101.

When inserting the syringe needle holder 109 into the injection liquid outlet tube 106 formed in the adapter tube 105, the syringe needle holder 109 can be directly inserted into the injection liquid outlet tube 106. The injection liquid outlet tube 106 is fixed into the adapter tube 105 by interference fit. Therefore, when injecting the injection liquid, the injection liquid does not leak between the injection liquid outlet tube 106 and the syringe needle holder 109. In addition, the oval flange 109a is formed on the back end outer surface of the syringe needle holder 109. It is preferable that the oval flange 109a is connected to the spiral projection 102a formed in a spiral shape on the inner circumference of the coupling tube 102 formed on the fore end of the cylinder and having a step difference.

The process step of fixing the syringe needle holder 109 having the syringe needle 108 fixed thereto to the injection liquid outlet tube 106 of the adapter tube 105 can also be performed during the first assembly step of the disposable syringe according to the present invention. However, since the assembly step is not limited to only a single method, the present invention is advantageous in that the above-described process step can be alternatively performed during a process step prior to the actual usage of the disposable syringe. Finally, the protective cap 110 is fixed to the syringe needle holder 109, thereby protecting the syringe needle 108 from external contact.

FIGS. 9A to 9F illustrate cross-sectional views showing usage steps of the disposable syringe according to the first embodiment of the present invention.

In order to inject the injection liquid into the patient, the empty space of the cylinder should first be filled with the injection liquid. However, this process step is identical to that described in the related art, and will, therefore, be omitted for simplicity. FIG. 9A illustrates the cylinder being filled with the injection liquid, shown as the left side of the piston 104 fixed to the plunger 103.

The process step of injecting the injection liquid into the patient is also identical to that described in the related art, and will, therefore, be also omitted for simplicity. However, in the present invention, during the injection process, due to the insertion tube 107, the airtight condition is maintained between the cylinder 101 and the adapter tube 105, which is fixed at the fore end of the cylinder 101. Accordingly, the injection liquid flowing out of the cylinder 101 is flown through the injection liquid outlet tube 106 formed in the adapter tube 105 to be drawn out of the syringe.

FIGS. 8 and 9B illustrate the completion of the injection of the injection liquid to the patient.

Referring to FIGS. 8 and 9B, the inclined projected part 104a of the piston 104 is accurately accommodated into the inclined hollow part 107e of the insertion tube 107. In other words, during the injection process, when pressure is applied to the inner circumference of the cylinder 101, the injection liquid within the cylinder 101 naturally flows down to the center along the inclined hollow part 107e of the insertion tube 107. Then, the injection liquid easily flows through the insertion tube 107 to be squeezed out of the cylinder 101 without any residue remaining.

Meanwhile, the pressurization part 112 formed at the central portion at the fore end of the plunger 103 is inserted and fixed to the inner circumference of the injection liquid outlet tube 106 of the adapter tube 105 through the inner circumference of the insertion tube 107. Then, the edge of the inclined horizontal center point of the pressurization part 112 presses a specific portion of the injection liquid outlet tube 106. In other words, the pressurization part 112 applies an eccentric pressure to a specific contact point of the injection liquid outlet tube 106.

Figure 9C:
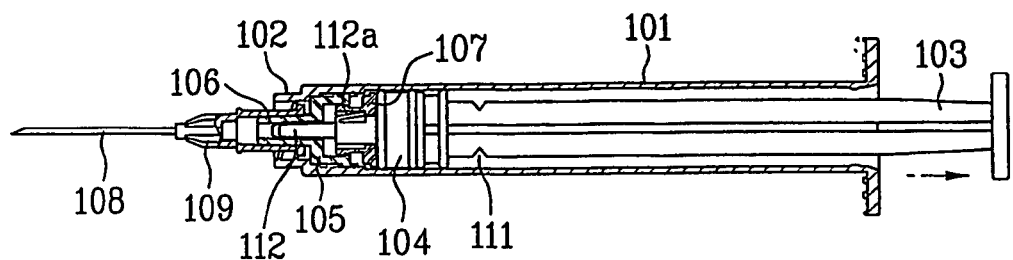

FIG. 9C illustrates the process step of releasing the airtight condition between the cylinder and the adapter tube.

Referring to FIG. 9C, when the injection is completed, the user pulls the cylinder 101 in a direction opposite to the patient in order to pull out the syringe needle 108 from the patient's skin. And, by pulling the plunger 103 backwards towards the back end of the cylinder 101, the pressurization part 112 formed on the plunger 103 is also pulled backwards. The first projection 112a formed on the outer circumference of the pressurization part 112 is connected to the first connecting part 107a formed along the inner circumference of the insertion tube 107. Accordingly, the moving force applied to the back end of the plunger 103 is transmitted to the insertion tube 107 through the first projection 112a, thereby allowing the insertion tube 107 to move slightly to the outside of the inner circumference of the adapter tube 105. In other words, the movement is allowed within a gap formed between the inner circumference of the adapter tube and the outer circumference of the insertion tube. Therefore, the pressure applied by the insertion tube 107 from the adapter tube 105 towards the cylinder 101 is released, and so, the airtight contact between the adapter tube 105 and the cylinder 101 is also released. However, if there is no gap formed between the inner circumference of the adapter tube 105 and the outer circumference of the insertion tube 107, the airtight condition between the adapter tube 105 and the cylinder 101 cannot be easily released. This is because a friction is applied to the entire contacting surface between the cylinder 101 and the adapter tube 105, when the plunger 103 is pulled backwards. However, since the gap between the adapter tube 105 and the insertion tube 107 is formed in the present invention, a force sufficient for overcoming the friction between the adapter tube 105 and the insertion tube 107 is required when releasing the airtight condition. More specifically, the adapter tube 105 and the insertion tube 107 have a relatively small contacting surface. Therefore, even though the two members are connected to each other by interference fit, the airtight condition between the cylinder 101 and the adapter tube 105 can be easily released.

Meanwhile, the connecting part can be formed along the inner circumference of the injection liquid outlet tube 106 contacting the edge of the pressurization part 112, and the projection can be formed at the edge of the pressurization part 112 closer to the fore end thereof as compared to the connecting part. Therefore, in a later process, as the plunger 103 is pulled backwards and moving backwards along with the pressurization part 112, the projection is connected to the connecting part, thereby applying a moving force to the injection liquid outlet tube 106 towards the back end of the syringe.

Figure 9D:
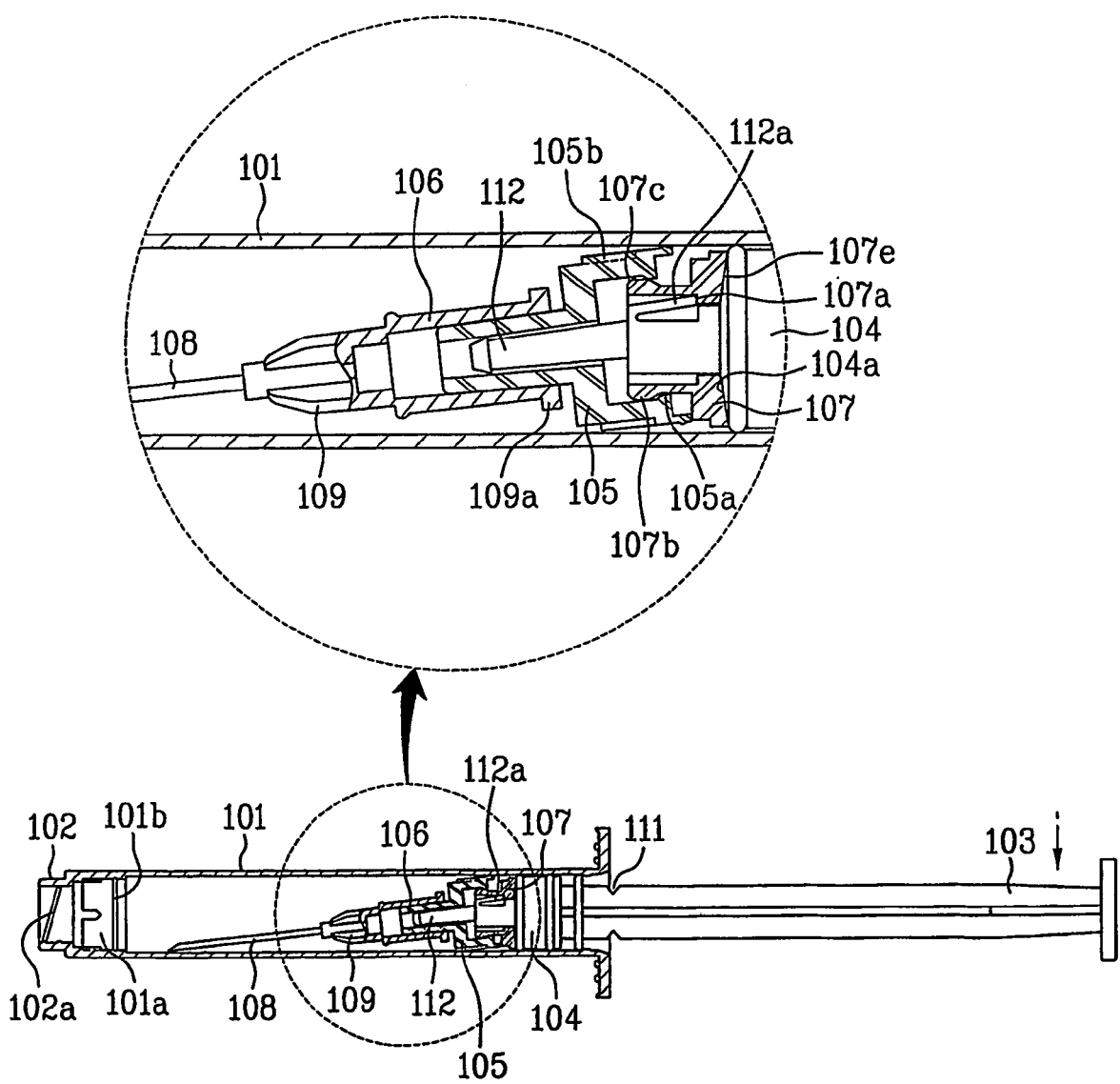

FIG. 9D illustrates the process step of pulling the syringe needle holder to the inside of the cylinder.

Referring to FIG. 9D, after releasing the airtight condition between the cylinder 101 and the adapter tube 105, the friction between the cylinder and the adapter tube is decreased considerably. Therefore, when the plunger 103 is pulled backwards, the syringe needle holder 109 can be easily brought inside the cylinder 101. A more detail description of the process will now follow. As the insertion tube 107 is moved backwards, the second projection 107b formed on the outer circumference of the insertion tube 107 is connected to the second connecting part 105a formed in the inner circumference of the adapter tube 105. Accordingly, the insertion tube 107 pulls the adapter tube 105 while moving towards the back end of the cylinder 101. At this point, since the syringe needle holder 109 is fixed to the injection liquid outlet tube 106 formed in the adapter tube 105, the syringe needle holder 109 is also pulled into the empty space of the cylinder 101. In other words, the syringe needle 108 is pulled onto the empty space of the cylinder 101 while being fixed to the syringe needle holder 109.

Meanwhile, when the syringe needle holder 109 is pulled into the empty space of the cylinder 101, the back end of the adapter tube 105 is spaced apart from the edge of the cylinder 101. And, the adapter tube 105 and the syringe needle holder 109 inserted in the injection liquid outlet tube 106 thereof is hung onto the outer edge of the insertion tube 107 inserted in the adapter tube 105. At this point, due to an eccentric center of gravity, the fore end of the adapter tube 105 coupled to the syringe needle holder 109 is inclined downwards (i.e., towards the gravitational direction).

In addition, due to the pressurization part 112 formed on the edge of the plunger 103, a pressure is applied on the adapter tube 105 coupled to the syringe needle holder 109 towards the gravitational direction. As described above, when the injection process is completed, the edge of the pressurization part 112 having an inclined horizontal center point presses a specific contacting point of the injection liquid outlet tube 106. Thereafter, since the pressurization part 112 is formed of an elastic material, when the plunger 103 is pulled backwards, a recovery force is applied to the gravitational direction, thereby pressing the coupled body. At this point, a force is applied as the first projection 112a formed on the outer circumference of the pressurization part 112 is connected to the first connecting part 107a. The force applied to the first projection 112a is also transmitted to the pressurization part 112, thereby pressing the coupled body downwards (i.e., towards the gravitational direction). Therefore, the adapter tube 105 coupled to the syringe needle holder 109 is inclined downwards, as the coupled body is hung onto the outer edge of the insertion tube 107. More specifically, only the fore end of the syringe needle 108 fixed to the syringe needle holder 109 comes into contact with the inner surface of the cylinder 101. Therefore, a constant inclination angle is maintained between the contacting surface of the cylinder 101 and the syringe needle 108 fixed to the syringe needle holder 109.

Figure 9E:
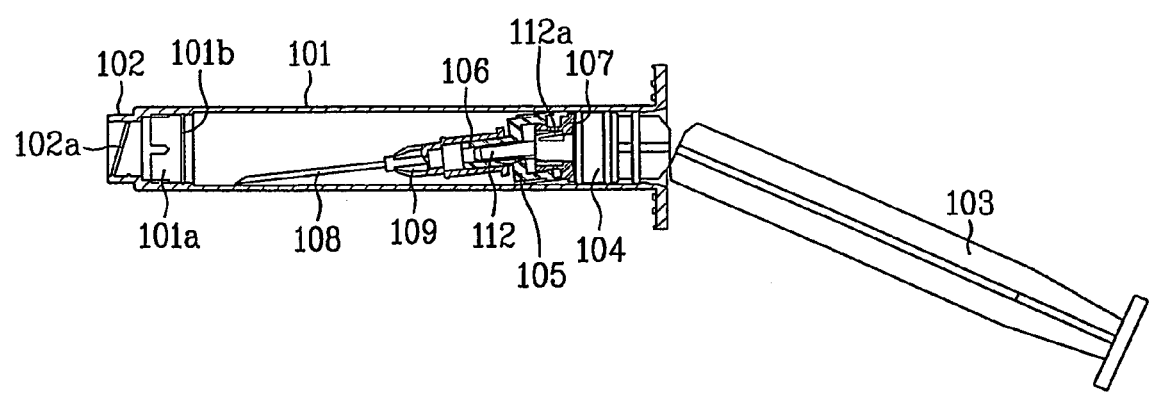
Figure 9F:
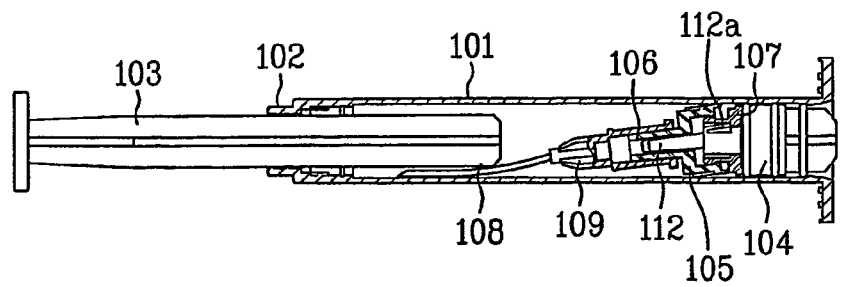

FIGS. 9E and 9F illustrate process steps of preventing the syringe needle holder from being extracted from the cylinder. However, the process steps are identical to those of the related art disposable syringe, and the description of the steps will, therefore, be omitted for simplicity.

Figure 11:
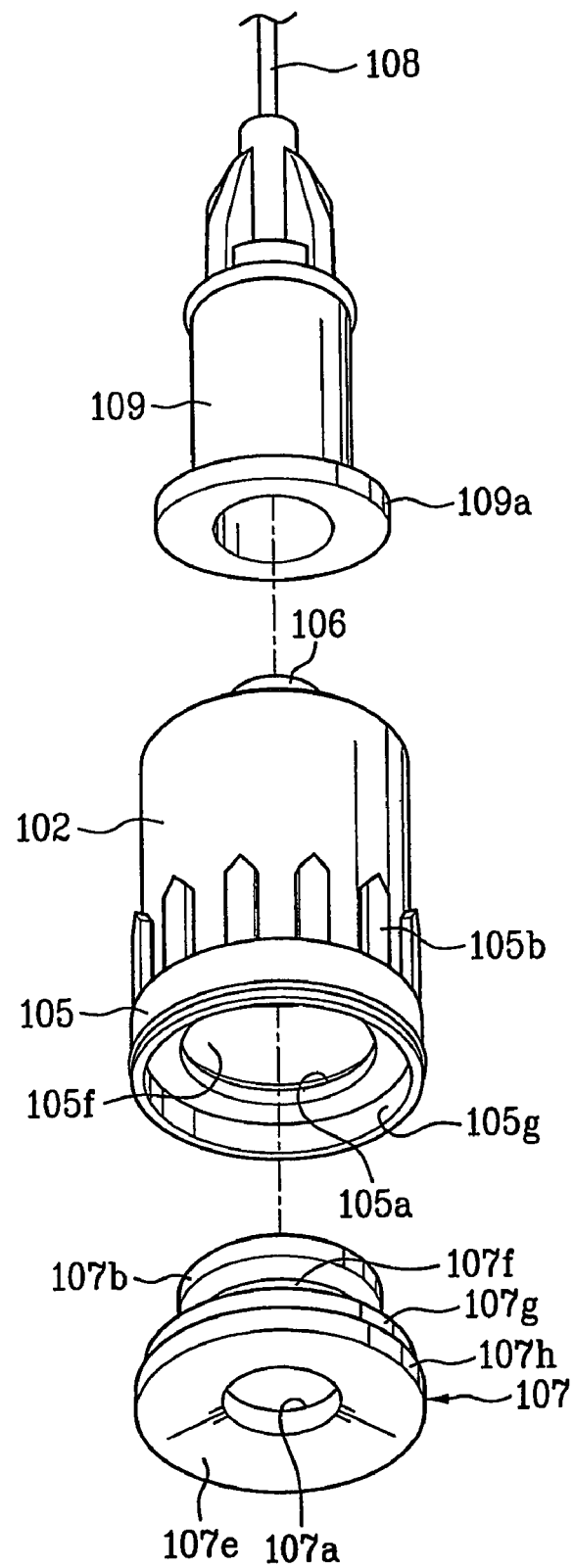
FIG. 11 illustrates a perspective view of the main parts of the disposable syringe according to the second embodiment of the present invention.
Figure 12:
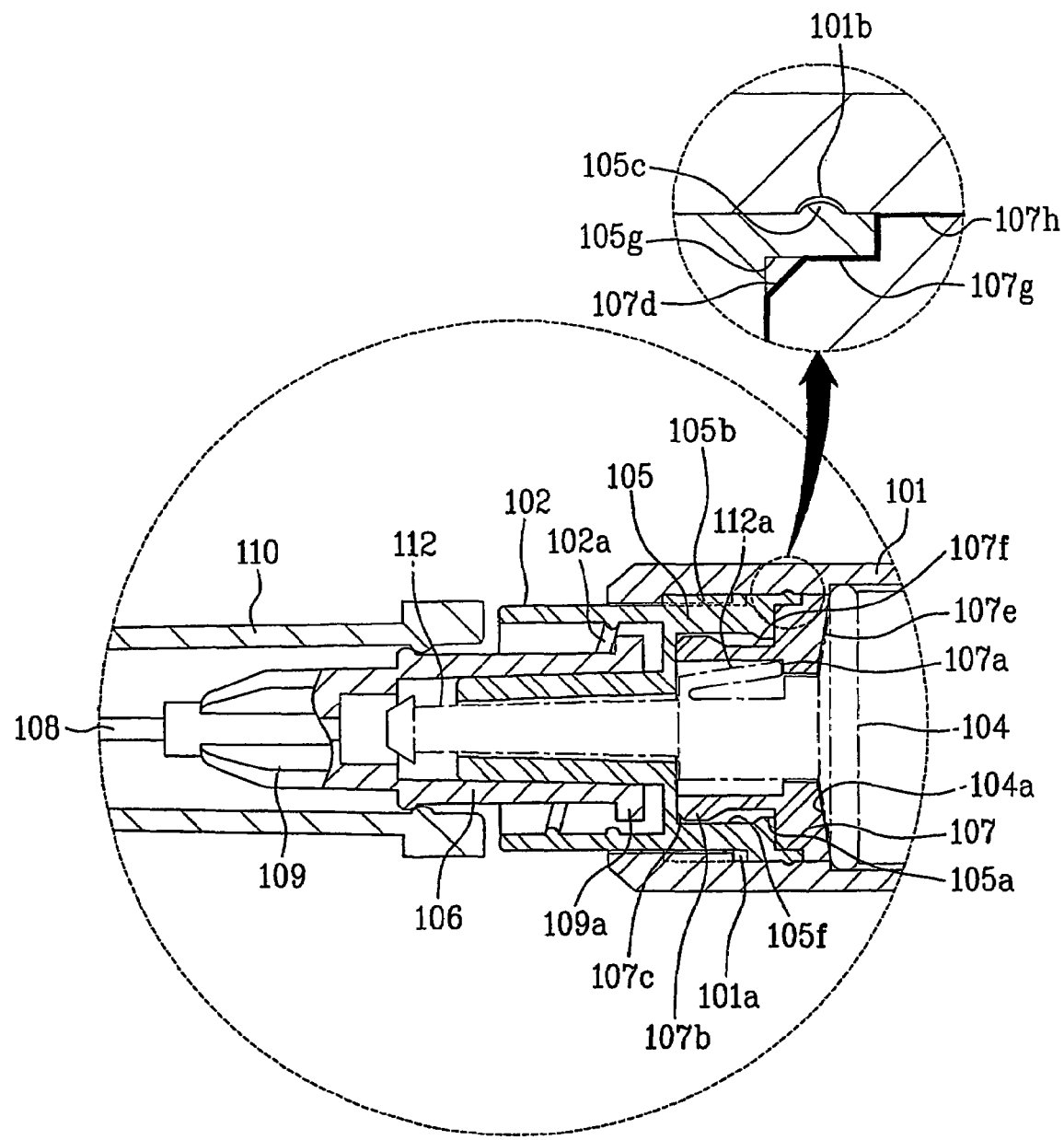
FIG. 12 illustrates a cross-sectional view of the main parts of the disposable syringe according to the second embodiment of the present invention.

The disposable syringe according to a second embodiment of the present invention will now be described in detail with reference to FIGS. 10 to 12.

Figure 10:
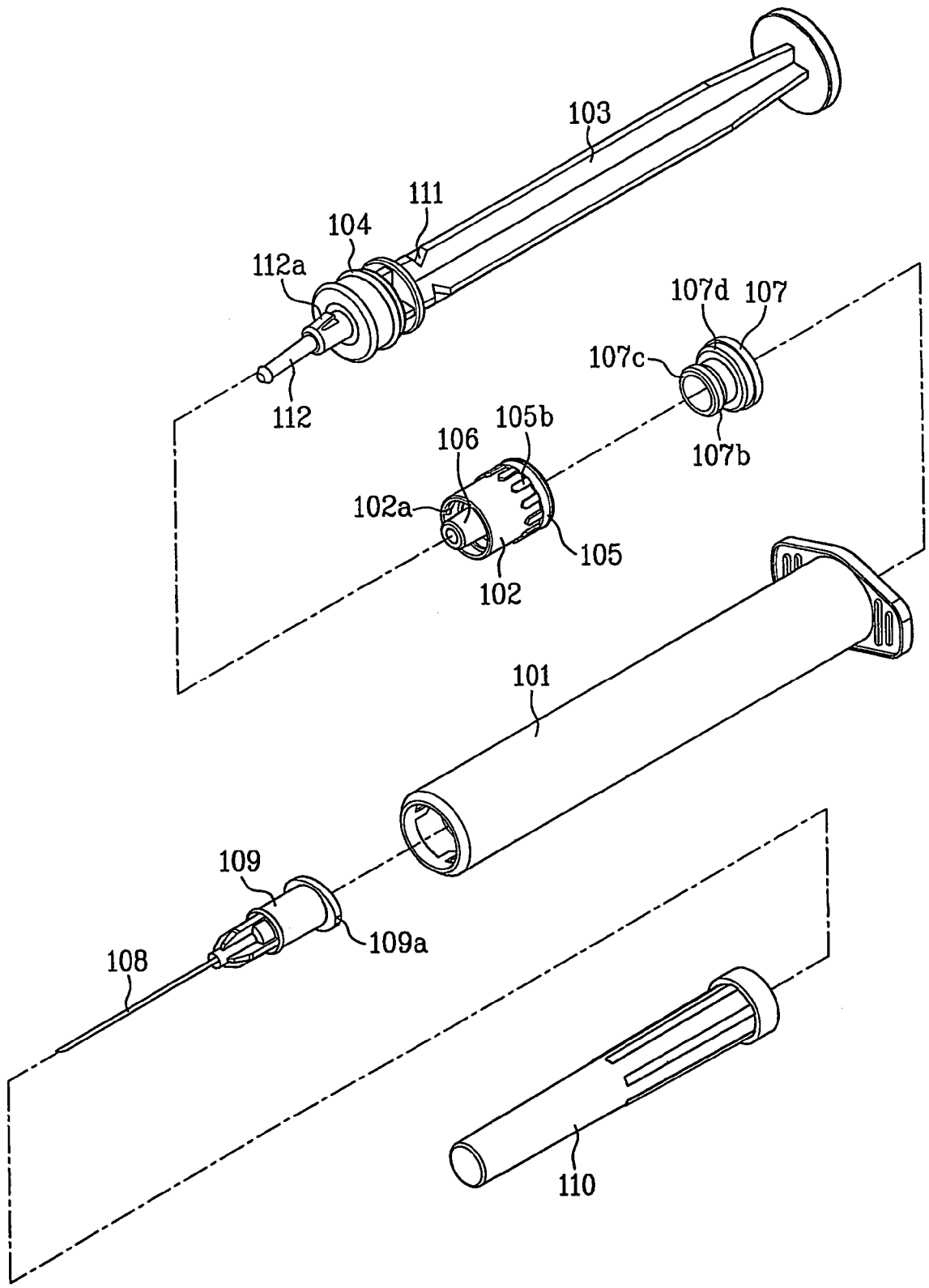
FIG. 10 illustrates an exploded view of a disposable syringe according to a second embodiment of the present invention.

FIG. 10 illustrates an exploded view of a disposable syringe according to the second embodiment of the present invention. FIG. 11 illustrates a perspective view of the main parts of the disposable syringe according to the second embodiment of the present invention. And, FIG. 12 illustrates a cross-sectional view of the main parts of the disposable syringe according to the second embodiment of the present invention.

Referring to FIG. 10, the disposable syringe according to the second embodiment of the present invention includes a cylinder 101 having both ends open, an adapter tube 105 being inserted within the cylinder 101, and an insertion tube 107 being inserted within the adapter tube 105. The disposable syringe also includes a piston 104, a plunger 103 having a pressurization part 112 formed on the edge thereof, and a syringe needle holder 109 being fixed to a coupling tube 102.

Unlike in the first embodiment of the present invention, in the disposable syringe according to the second embodiment of the present invention, the coupling tube 102 having the syringe needle holder 109 fixed thereon is not formed on the cylinder 101, but formed directly on the adapter tube 105. In other words, only the structures of the cylinder 101 and the adapter tube 105 are different as compared to the first embodiment of the present invention. Therefore, the process steps of using the disposable syringe and the assembly process steps are identical to those described in the first embodiment, and the descriptions of the second embodiment will, therefore, be omitted for simplicity.

The above-described disposable syringe according to the present invention has the following advantages.

An adapter tube and an insertion tube of the present invention are not easily deformed when having an external pressure applied thereon. Also, the adapter tube and the insertion tube are accurately placed within the cylinder of the syringe so as to provide stability of the assembly, thereby reducing product deficiency.

Also, auxiliary fabrication devices are not required in the fabrication line in order to reduce deficiency in disposable syringes, thereby reducing the fabrication cost.

Finally, if any, the deficiency of the adapter tube and the insertion tube can be easily detected through the naked eye upon the assembly process of the disposable syringe. And so, an intact assembly prevents injection liquid from leaking out of the disposable syringe, thereby increasing product reliability.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A disposable syringe, comprising:
a cylinder having both ends open;
an adapter tube inserted into one side of the cylinder in substantially airtight contact with an inner circumference thereof;
an injection liquid outlet tube at the fore end of the adapter tube;
a needle held by a syringe needle holder coupled to the injection liquid outlet tube;
an insertion tube at least partially inserted into the adapter tube, the insertion tube having a first connecting part formed at an aft end of an inner circumference thereof;
a pressurization part inserted into and received by the injection liquid outlet tube and configured to pressure at least a tip of the needle against an inner surface of the cylinder when the needle is fully retracted into the cylinder and the pressurized part is inserted into the adapter tube, wherein the pressurization part has a projection part on an outer circumference thereof which directly contacts the first connecting part of the insertion tube when the pressurization part is inserted into the injection liquid outlet tube and also directly contacts the first connecting part when the substantially airtight contact is released between the cylinder and the adapter tube when the needle is fully retracted into the cylinder in a manner such that the pressurization part is still received by the injection liquid outlet tube.

2. The disposable syringe according to claim 1, wherein the adapter tube includes a small diameter part, and a large diameter part having an inside diameter relatively larger than the small diameter part, and wherein the insertion tube includes a first contacting part being in substantially airtight contact with an inner circumference of the large diameter part of the adapter tube, and an insertion part being inserted into the small diameter part.

3. The disposable syringe according to claim 2, further comprising a second contacting part extendedly formed at a back end of the first contacting part and contacting the inner circumference of the cylinder.

4. The disposable syringe according to claim 3, wherein a second connecting part is formed at the small diameter part of the adapter tube, and a second projection corresponding to the second connecting part of the adapter tube is formed at the insertion part of the insertion tube.

5. The disposable syringe according to claim 4, wherein the second projection of the insertion tube is formed only at a fore end portion of the insertion tube.

6. The disposable syringe according to claim 4, wherein the second projection of the insertion tube is formed to be inclined towards a fore end of the insertion tube.

7. The disposable syringe according to claim 2, wherein an outside diameter of the first contacting part of the insertion tube is larger than an inside diameter of the large diameter part of the adapter tube.

8. The disposable syringe according to claim 2, wherein a projection is formed on an outer circumference of the adapter tube, and a groove corresponding to the projection of the adapter tube is formed on the inner circumference of the cylinder.

9. The disposable syringe according to claim 2, wherein at least one of the adapter tube and the insertion tube is formed of an elastic material.

10. The disposable syringe according to claim 2, wherein a projected part is formed on the outer circumference of the adapter tube, and an insertion groove corresponding to the projected part of the adapter tube is formed on the inner circumference of the cylinder.

11. The disposable syringe according to claim 1, wherein a primary axis of pressurization part is formed at an angle to a primary axis of the cylinder to cause the tip of the needle to pressure against the inner surface of the cylinder.

12. The disposable syringe according to claim 1, wherein the pressurization part is formed of an elastic material.

13. The disposable syringe according to claim 1, wherein:
a coupling tube is formed at a fore end of the cylinder;
a coupling tube projection is formed on an inner circumference of the coupling tube; and
a flange corresponding to the coupling tube projection is formed on a the syringe needle holder.

14. The disposable syringe according to claim 1, wherein:
the cylinder comprises a plurality of fastening grooves formed on an inner circumference of the cylinder; and
the adapter tube comprises a plurality of fastening projections configured to fasten to the plurality of fastening grooves.

15. A disposable syringe comprising:
a cylinder having a plurality of fastening grooves formed on an inner circumference thereof;
an adapter tube received by the cylinder and including a small diameter part, and a large diameter part having an inside diameter relatively larger than the small diameter part, and a plurality of fastening projections spaced apart on the outer circumferential surface thereof which are inserted into the fastening grooves of the cylinder to form a substantially airtight interface between the adapter tube and the cylinder;
a needle holder received by the cylinder;
an injection liquid outlet tube formed at a distal end of the adapter tube and received by the needle holder;
an insertion tube received by the adapter tube, wherein the insertion tube includes a first contacting part being in substantially airtight contact with an inner circumference of the large diameter part of the adapter tube and an insertion part received by the small diameter part;
a plunger configured for receipt by the cylinder, the plunger having a piston formed at a fore end thereof and a pressurization part formed at a fore end of the piston, the pressurization part including a first pressurization part at a fore end thereof that is received by the injection liquid outlet tube and a second pressurization part at an aft end thereof that is received by the insertion tube and connected to the piston, the second pressurization part having a projection part which directly contacts the insertion tube at an inner surface thereof to cause a release of the substantially airtight contact between the cylinder and the adapter tube by transmitting a force from the plunger to the insertion tube when a moving force is applied to the plunger, wherein the first pressurization part is still received by the injection liquid outlet tube when the substantially airtight contact between the cylinder and the adapter tube is released.

16. A disposable syringe comprising:

a cylinder;

an adapter tube received by the cylinder in substantially airtight contact therewith, the adapter tube having a plurality of fastening projections spaced apart on the outer circumferential surface thereof that contact the inner surface of the cylinder when the adapter tube is received by the cylinder;

a needle holder that holds a needle, the needle holder being received by the cylinder;

an injection liquid outlet tube formed at a distal end of the adapter tube and which is received by the needle holder;

an insertion tube received by the adapter tube in a substantially in airtight contact therewith;

a piston received by the cylinder, the piston having a pressurization part at the distal end thereof that is received by the injection liquid outlet tube and configured to pressure at least a tip of the needle against an inner surface of the cylinder when the needle is fully retracted into the cylinder, the pressurization part includes including a projection part comprising a cantilever which directly contacts the insertion tube to cause a release of the substantially airtight contact between the cylinder and the adapter tube when the needle is fully retracted into the cylinder, wherein the pressurization part is still received by the injection liquid outlet tube when the substantially airtight contact between the cylinder and the adapter tube is released.

* * * * *